(12) United States Patent
Wen

(10) Patent No.: US 10,413,514 B2
(45) Date of Patent: Sep. 17, 2019

(54) CONTROLLED-RELEASE SOLID PREPARATION WITH PARTIAL COATING

(71) Applicant: Xiaoguang Wen, Taizhou (CN)

(72) Inventor: Xiaoguang Wen, Taizhou (CN)

(73) Assignee: OVERSEAS PHARMACEUTICALS, LTD., Taizhou (CN)

( * ) Notice: Subject to any disclaimer, the term of this patent is extended or adjusted under 35 U.S.C. 154(b) by 0 days.

(21) Appl. No.: 15/302,977

(22) PCT Filed: Apr. 8, 2015

(86) PCT No.: PCT/CN2015/076028
§ 371 (c)(1),
(2) Date: Oct. 7, 2016

(87) PCT Pub. No.: WO2015/154656
PCT Pub. Date: Oct. 15, 2015

(65) Prior Publication Data
US 2017/0027872 A1 Feb. 2, 2017

(30) Foreign Application Priority Data

Apr. 8, 2014 (CN) .......................... 2014 1 0139563

(51) Int. Cl.
| | | |
|---|---|---|
| *A61K 9/24* | (2006.01) | |
| *A61K 9/20* | (2006.01) | |
| *A61K 9/28* | (2006.01) | |
| *A61K 31/192* | (2006.01) | |
| *A61K 31/381* | (2006.01) | |
| *A61K 31/4045* | (2006.01) | |
| *A61K 31/496* | (2006.01) | |
| *A61K 31/53* | (2006.01) | |
| *A61K 31/573* | (2006.01) | |

(52) U.S. Cl.
CPC ............. *A61K 9/209* (2013.01); *A61K 9/20* (2013.01); *A61K 9/205* (2013.01); *A61K 9/2009* (2013.01); *A61K 9/2013* (2013.01); *A61K 9/2018* (2013.01); *A61K 9/2022* (2013.01); *A61K 9/2054* (2013.01); *A61K 9/2086* (2013.01); *A61K 9/2095* (2013.01); *A61K 9/282* (2013.01); *A61K 9/2813* (2013.01); *A61K 9/2826* (2013.01); *A61K 9/2866* (2013.01); *A61K 9/2893* (2013.01); *A61K 31/192* (2013.01); *A61K 31/381* (2013.01); *A61K 31/4045* (2013.01); *A61K 31/496* (2013.01); *A61K 31/53* (2013.01); *A61K 31/573* (2013.01)

(58) Field of Classification Search
CPC .. A61K 2300/00; A61K 31/00; A61K 31/135; A61K 31/137; A61K 45/06; A61K 9/209; A61K 31/138; A61K 31/155; A61K 31/164; A61K 31/381; A61K 31/40; A61K 31/4015; A61K 31/4178; A61K 31/4415; A61K 9/006; A61K 9/0065; A61K 9/0068; A61K 9/0092; A61K 9/2027; A61K 9/2031; A61K 9/2054; A61K 9/2077; A61K 9/28; A61K 9/2846; A61K 9/2853; A61K 9/2866; A61K 9/2886; A61K 9/4808; A61K 9/2018
See application file for complete search history.

(56) References Cited

U.S. PATENT DOCUMENTS

| | | | | |
|---|---|---|---|---|
| 5,593,694 | A * | 1/1997 | Hayashida | ........... A61K 9/2054 424/464 |
| 5,922,342 | A * | 7/1999 | Shah | ..................... A61K 9/006 424/438 |
| 6,264,985 | B1 | 7/2001 | Cremer | |
| 2005/0013863 | A1 * | 1/2005 | Lim | ..................... A61K 9/0065 424/472 |
| 2008/0200508 | A1 * | 8/2008 | Rariy | .................. A61K 9/2886 514/321 |

FOREIGN PATENT DOCUMENTS

| | | | | |
|---|---|---|---|---|
| CN | 101843598 A | * | 6/2010 | ............. A61K 47/38 |
| CN | 102614141 | | 8/2012 | |
| CN | 102614141 A | * | 8/2012 | ............... A61K 9/20 |
| WO | WO-1996/007401 | | 3/1996 | |
| WO | WO-2005/013935 | | 2/2005 | |
| WO | WO2005/013935 A2 | * | 2/2005 | ............... A61K 9/00 |
| WO | WO2005013935 A2 | * | 2/2005 | ............... A61K 9/00 |
| WO | WO-2008/006216 | | 1/2008 | |
| WO | WO-2009/002846 | | 12/2008 | |
| WO | WO-2015/191920 | | 12/2015 | |

OTHER PUBLICATIONS

CN102614141A translation. (Year: 2012).*
CN101843598 translation (Year: 2010).*
International Search Report and Written Opinion for PCT/CN2015/076028, dated Jul. 17, 2015, 17 pages (English translation included).

* cited by examiner

*Primary Examiner* — Audrea B Coniglio
(74) *Attorney, Agent, or Firm* — Gokalp Bayramoglu

(57) ABSTRACT

Disclosed is a controlled-release solid preparation, which consists of an internal core and a coating layer, wherein part of the surface of the internal core is not covered with the coating, and is exposed to the surface of the solid preparation. Since the medicament just releases at the exposed part, the aim of controlled release can be achieved by controlling this exposed surface area.

17 Claims, 5 Drawing Sheets

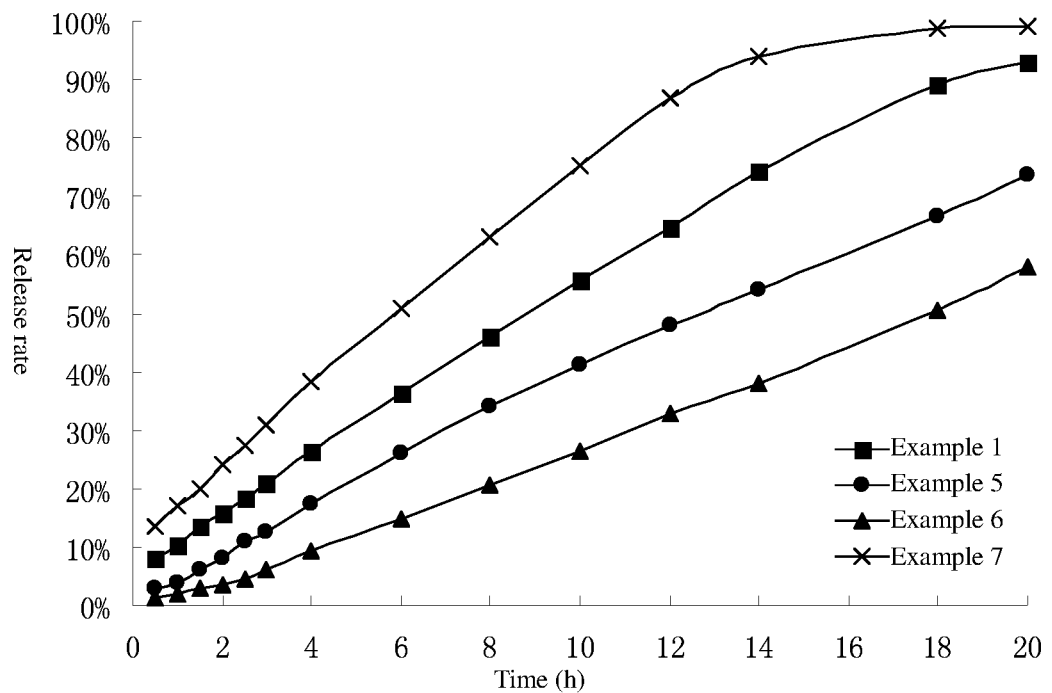
Figure 8
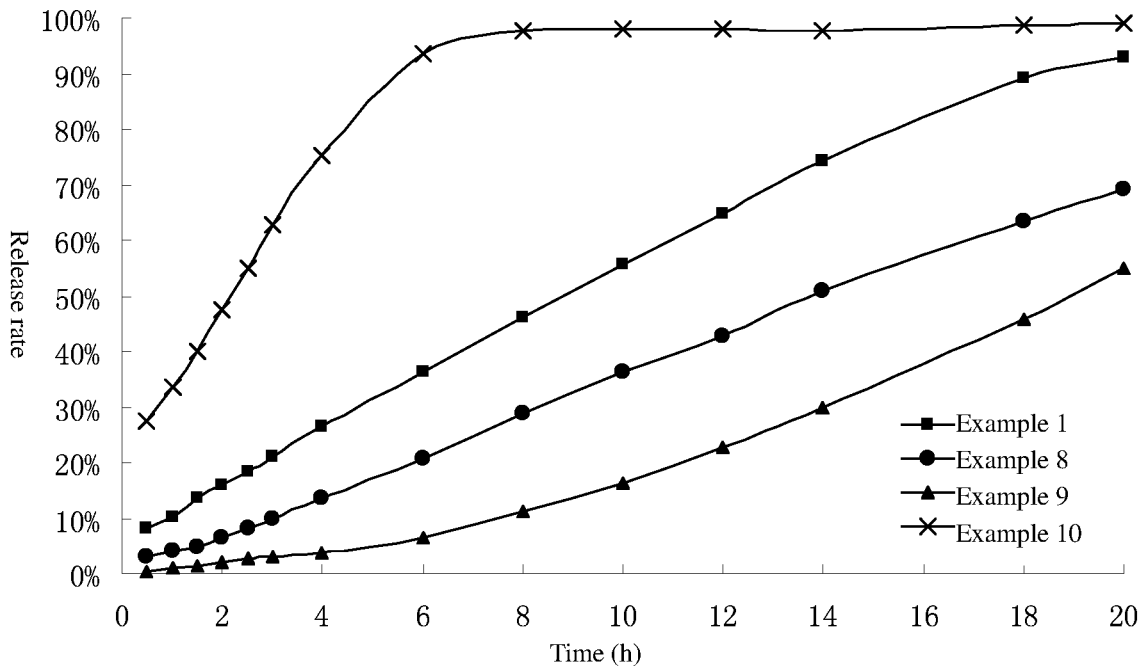
Figrue 9

CONTROLLED-RELEASE SOLID PREPARATION WITH PARTIAL COATING

The present application is a U.S. national phase of International Patent Application No. PCT/CN2015/076028, filed Apr. 8, 2015, which claims priority benefit to Chinese Patent Application No. 201410139563.9, filed on Apr. 8, 2014, the disclosures of which are incorporated by reference herein in their entireties for all purposes.

TECHNICAL FIELD

This invention belongs to pharmaceutical technology field, relates to a partially coated controlled-release solid preparation.

BACKGROUND ART

With regard to sustained-release and controlled-release solid preparation, it's common to adopt the method that active medicine is coated with sustained-release and/or controlled-release material. However, this method sometimes cannot achieve the expected medicine release effect. For example, it's difficult to realize in prior art that multi medicine's active ingredients can release in different speed at the preconceived time point. The ideal medicine release method should be that, different release behaviors are obtained by pulse type drug delivery, especially in the way of exponential release from slow to fast. Current preparations cannot achieve this effect. Therefore, it's required to change structure of preparation to achieve the purpose of controlling the release behavior.

DISCLOSURE OF THE INVENTION

Goal of this invention is to provide a new-structural controlled-release solid preparation, which makes medicine's active ingredients can release in pulse pattern in different speed at the preconceived time point, so as to achieve ideal controlled release effect.

This invention designs a new structural solid medicine preparation, and technical solution is as follows:

A controlled-release solid preparation, consists of inner core and coating layer, said inner core contains active medicine and adjuvant, said coating layer contains coating material and, said coating layer contains or does not contain active ingredients, characterized in that, partial surface of said inner core is not coated by coating layer, and is exposed to surface of solid preparation.

That is, coating layer of preparation of this invention does not completely coat said inner core, and part of said inner core surface is exposed to surface of solid preparation.

In solution of this invention, since part of medicine inner core is exposed, it's convenient to control medicine release of inner core through this part.

Said exposed part, its position, area and shape is unlimited; in practical application, it's available to design different shapes of each preparation, based on release requirement of specific active ingredient of preparation and in view of being convenient for preparation production.

Said inner core is one layer or multi-layers, and said layer is one layer of or layers of sustained release layer, or meantime contains rapid release layer and sustained release layer.

When inner core is two or more layers, components of different layers release in sequence: outermost layer releases first, then the secondary outer layer releases, at last component of innermost layer of inner core releases. Through this pattern, it's available to control release sequence and release timing of different medicine.

Material of said sustained release layer is selected from one or several of the groups consisting of sodium alginate, methyl cellulose, hydroxyethyl cellulose, hydroxypropyl methyl cellulose, hydroxypropyl cellulose, povidone or polyethylene oxide.

Material of said coating layer is water-soluble or water-insoluble; said water-soluble coating material is selected from one or several of the groups consisting of hydroxypropyl methyl cellulose, hydroxypropyl cellulose; said water-insoluble coating material is selected from one or several of the groups consisting of ethyl cellulose, cellulose acetate polymer, acrylic resin.

Material of said coating layer can also contains water-soluble pore-forming agent, which is selected from one or several of the groups consisting of povidone, lactose, sodium chloride.

When above solid preparation is tablet, its inner core is tablet core consisting of one layer or more than one layer of tablet. Part of one bottom surface (can also be regarded as the top surface) is exposed without coating material coated (see also FIGS. 1, 2, 3).

The other solution of this invention is that, there is another coating layer on the outer surface of said coating layer, said coating layer contains or does not contain active ingredients.

Another solution of this invention is that, said coating layer is prepared by compression coating method.

Components of said inner core and coating layer also include pharmaceutic adjuvants, which is selected from conventional pharmaceutical preparations, such as, filler, disintegrating agent, lubricant, flow aid, etc. It's available to select according to requirements of this field technology. For example, filler is selected from one or several of the groups consisting of lactose, Pregelatinized Starch or microcrystalline cellulose; disintegrating agent is selected from one or several of the groups consisting of sodium carboxymethyl cellulose, cross-linked sodium carboxymethyl cellulose, sodium carboxymethyl starch or Crospovidonum; lubricant is selected from one or several of the groups consisting of stearic acid, magnesium stearate or talcum powder; flow aid is micro powder silica gel, etc.

When solid preparation of this invention is tablet, tablet pressing is performed in tablet press machine by using two different model number of punch pin, with following steps:

1) Mix all the components for preparing tablet core, and the first pressing is performed by using model number I punch pin to obtain tablet core;

2) model number II punch pin is used to replace model number I punch pin and, after mix all the components for preparing tablet coating layer, fill in middle module;

3) filling the tablet core prepared in step 1) in the center of middle module and performing the second pressing, and the solid preparation is obtained;

Diameter of said model number I punch pin is less than that of model number II punch pin.

In above method, said step 2) and 3) are as follows:

after model number I punch pin is replaced with model number II punch pin, tablet core prepared in step 1) is firstly filled in the center of middle module, and then the uniformly mixed coating layer components are filled around tablet core in middle module to perform the second pressing.

This invention has following technical effects:

Because medicine release surface is only in the exposed position, it's available to achieve goal of controlled-release by controlling surface area of the exposed position. Furthermore, since medicine does not release from the unexposed position, the effect of constant-speed release can be achieved.

When inner core is two or more layers, components of different layers release in sequence: outermost layer releases first, then the secondary outer layer releases, at last component of innermost layer of inner core releases. Through this pattern, it's available to control release sequence and release timing of different medicine.

In preparation of this invention, multiple medicine active ingredients are released in different speed at different time point, by controlling amount of active ingredient of each layer in inner core and amount as well as types of sustained release material, and by controlling amount as well as types of active ingredient as well as sustained-release/controlled-release materials of pressed coating layer and amount of active ingredient, so as to realize pulse type drug delivery and to acquire different release behavior, e.g., zero order release, first order release, especially exponential release from slow to fast.

BRIEF DESCRIPTION OF THE DRAWINGS

It's demonstrated from above curves that, by adopting preparation method of this invention, FIG. 4: medicine in vitro dissolution is changed to zero order release from first order release; FIG. 5: that medicine is firstly sustained released slowly and then released rapidly can be realized; FIG. 6: that medicine release speed is gradually fastened can be realized; FIG. 7: at different stage that medicine is released slowly in different speed and released in a constant speed at each stage can be realized;

FIG. 8 is dissolution curves comparison among sustained release tablets in example 1, example 5, example 6, example 7; it's can be seen that, the more content of soluble material—lactose in coating is, the faster coating dissolution speed is;

FIG. 9 is dissolution curves comparison among sustained release tablets in example 1, example 8, example 9, example 10; it's can be seen that, the more content of sustained release material in inner core is, the slower inner core dissolution speed is;

EMBODIMENTS

Detecting method of medicine dissolution in this invention is as follows: according to XD dissolution rate determination $1^{st}$ method (for sustained release, controlled release, delay release preparations) recorded in Chinese Pharmacopoeia 2010 edition volume II appendix, tablet is put into 900 ml 0.1 mol/L hydrochloric acid solution, basket method, 100 round/minute, 37° C., pipette the appropriate amount of dissolution liquid at the specified sampling point to calculate the cumulative release rate of tablet, and drawing dissolution curve.

Example 1

Controlled Release Preparation with One Layer of Inner Core (Only Having One Sustained Layer)

Figure 1:
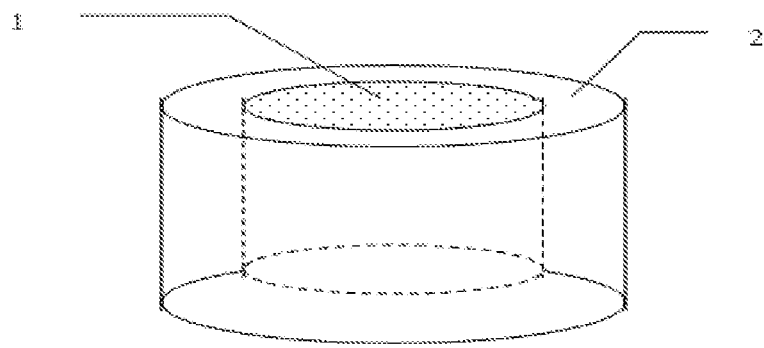
FIG. 1 is a structural diagram of controlled release tablet with monolayer of inner core, wherein, 1 is inner core, 2 is coating.

Preparation includes inner core and coating outside the inner core, and said inner core is mono-layer with only one sustained release layer. As shown in FIG. 1, part of inner core top surface is not coated by coating, and is exposed to surface of solid preparation.

Components and contents are as follows: 1000 tablets in total, each tablet weigh 800 mg.

| Inner core | |
|---|---|
| ibuprofen | 75 g |
| hydroxypropyl methyl cellulose K100LV | 75 g |
| Methyl cellulose | 15 g |
| lactose | 129 g |
| magnesium stearate | 3 g |
| micro powder silica gel | 3 g |
| In total | 300 g |

| Coating | |
|---|---|
| ethyl cellulose | 390 g |
| lactose | 100 g |
| magnesium stearate | 5 g |
| micro powder silica gel | 5 g |
| In total | 500 g |

Preparation Method:

1. Raw materials of inner core are weighed according to above prescription, and mixed completely for the next step; two model numbers of punch pin are selected, and diameter of said model number I punch pin is less than that of model number II punch pin;

2. Rotary tablet press machine is used with model number I punch pin installed; filling depth and pressing force of tablet press machine are adjusted for pressing inner core; weight of inner core is 300 mg per piece, and inner core hardness is 90N;

3. Adjuvants for coating are weighed according to prescription, and mixed completely for the next step;

4. Rotary tablet press machine is used with model number II punch pin installed; process parameters of tablet press machine are adjusted; the pressed inner core is put in center of stamping die; then the mixed coating materials are filled for pressing tablet, to make bottom surfaces of bottom and side of inner core are coated by coating materials; total weight of tablet is 800 mg, and hardness is 100N.

Figure 4:
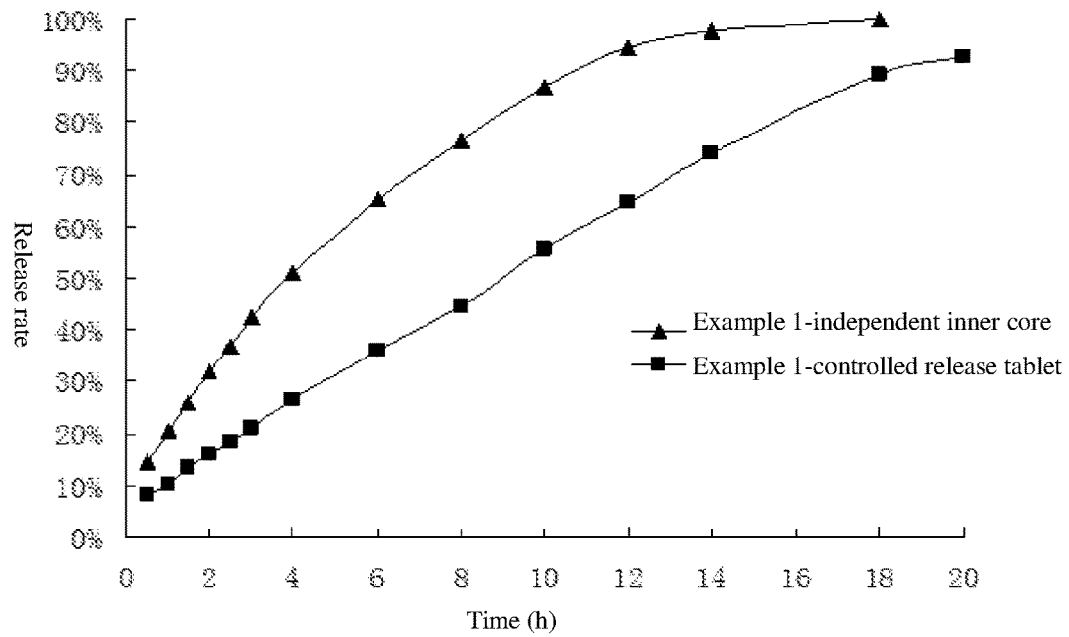
FIGS. 4-7 are dissolution curves comparisons between inner core and controlled release tablet include same inner core prepared by method of this invention respectively in examples 1-4. It's can been seen that, although inner core is same, after controlled release preparation having coating layer with partially exposed inner core is prepared, release behavior is obviously different, which is easy to meet various clinical medication requirements.

Medicine dissolution is detected, and dissolution curve is shown in FIG. 4. It's can be seen from FIG. 4 that, inner core release shows trend of first order release; after controlled-release tablet is prepared by adding outer coating, tablet release shows constant speed.

In example 1, only top surface of inner core is exposed to outside; during the process of dissolution, effective ingredients in inner core is released only through top surface; release area is constant, so zero order release effect can be achieved. Medicine model prepared in example 1 is propitious as the cardiovascular and cerebrovascular medicines, which can substitute for osmotic pump technology to achieve the goal of constant medicine release.

Example 2

Controlled Release Preparation with Inner Core of Two Layers (Sustained Release Layer and Rapid Release Layer)

Figure 2:
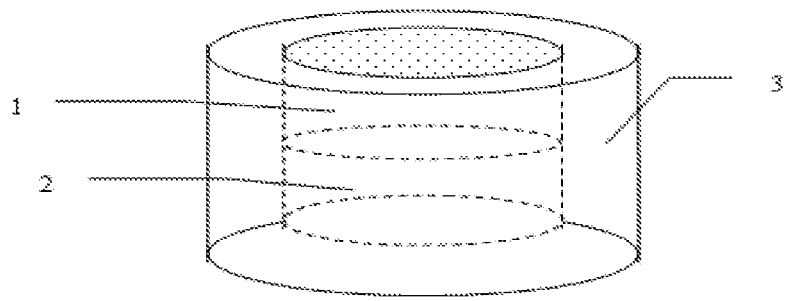
FIG. 2 is a structural diagram of controlled release tablet with a double layer tablet as inner core, wherein, 1 is inner core-sustained release layer; 2 is inner core-rapid release layer; 3 is coating.

Preparation includes inner core and coating outside the inner core, and said inner core is double layer tablet. As shown in FIG. 2, part of inner core top surface is not coated by coating, and is exposed to surface of solid preparation.

Components and contents are as follows: 1000 tablets in total, each tablet weigh 800 mg.

| Inner core-sustained release layer | |
| --- | --- |
| prednisolone acetate | 20 g |
| hydroxypropyl methyl cellulose K4M | 60 g |
| lactose | 116 g |
| magnesium stearate | 2 g |
| micro powder silica gel | 2 g |

| Inner core-rapid release layer | |
| --- | --- |
| prednisolone acetate | 10 g |
| lactose | 40 g |
| microcrystalline cellulose | 44 g |
| cross-linked sodium carboxymethyl cellulose | 5 g |
| lemon yellow | 0.3 g |
| magnesium stearate | 0.7 g |
| In total | 300 g |

| Coating | |
| --- | --- |
| ethyl cellulose | 390 g |
| lactose | 100 g |
| magnesium stearate | 5 g |
| micro powder silica gel | 5 g |
| In total | 500 g |

Preparation Method:

1. Raw materials of inner core-sustained release layer, inner core-rapid release layer are weighed according to above prescription, and mixed completely for the next step; two model numbers of punch pin are selected, and diameter of said model number I punch pin is less than that of model number II punch pin;

2. Rotary tablet press machine is used with model number I punch pin installed; filling depth and pressing force of tablet press machine are adjusted for pressing inner core; weight of inner core-sustained release layer is 200 mg per piece, weight of inner core-rapid release layer is 100 mg per piece, and inner core hardness is 80N;

3. Adjuvants for coating are weighed according to prescription, and mixed completely for the next step;

4. Rotary tablet press machine is used with model number II punch pin installed; process parameters of tablet press machine are adjusted; the pressed inner core with the colored rapid release layer upwards is put in center of stamping die; then the mixed coating materials are filled for pressing tablet, to make bottom surfaces of bottom and side of inner core are coated by coating materials; total weight of tablet is 800 mg, and hardness is 100N.

Figure 5:
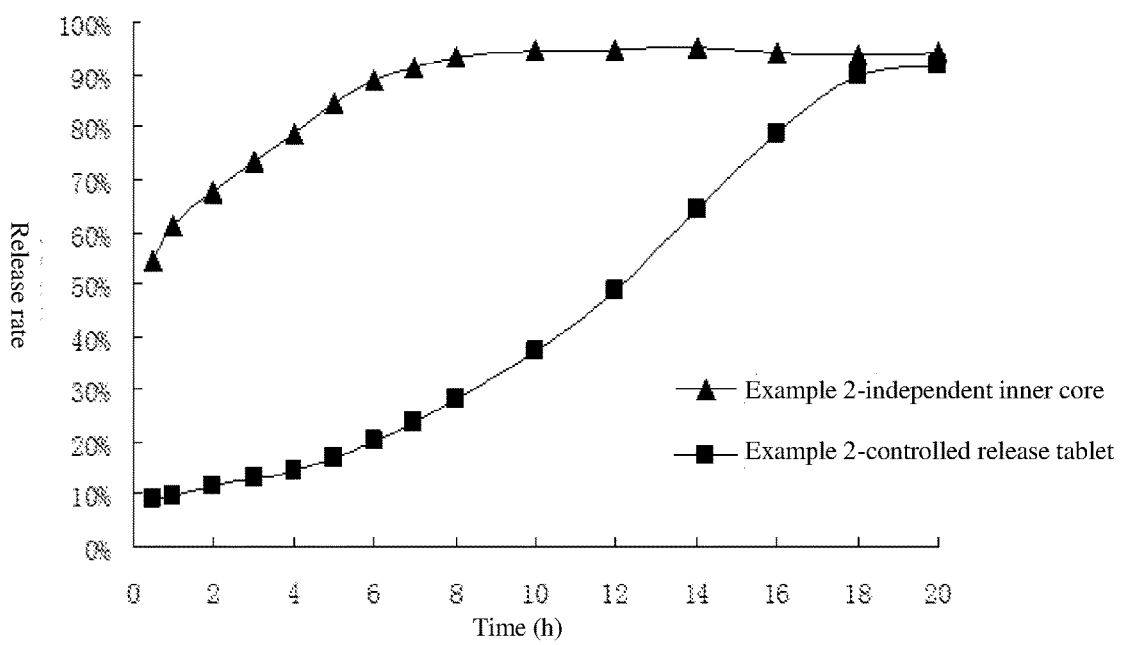

Medicine dissolution is detected, and dissolution curve is shown in FIG. 5. It's can be seen from FIG. 5 that, independent inner core disintegrates rapidly due to rapid-release layer with rapid dissolution speed, 90% of its medicine dissolution only takes 6 hours. After controlled-release tablet with coating is prepared, its dissolution shows release trend of first slow and then fast.

In example 2, inner core consists of double layers of sustained release layer, rapid release layer. During the process of dissolution, sustained release part in inner core dissolves firstly with active ingredients in sustained release layer releasing slowly; after sustained release layer releases completely, rapid release layer disintegrates rapidly, so as to achieve the goal of rapid medicine delivery.

Medicine model prepared in example 2 is propitious as medicine for treating those diseases which outbreak easily in the early morning, like morning stiffness, myocardial infarction, etc. the release time of rapid release layer is controlled at 4-6 hours after taking medicine, and that patients take medicine before sleeping can avoid disease outbreak in the early morning. In addition, medicine model prepared in example 2 is propitious as medicine which can be absorbed smoothly in stomach and absorbed poorly in the lower part of stomach. In environment of low pH value, medicine release slowly, and the released part can be absorbed as well as utilized basically; when pH value is enhanced, medicine solubility decreases, medicine absorption of organism reduces; at this time, to increase medicine release amount can remedy the problem of low bioavailability.

Example 3

Controlled Release Preparation with One Layer of Inner Core (Only Having One Sustained Layer)

Preparation includes inner core and coating outside the inner core, and said inner core is monolayer with only one sustained release layer. As shown in FIG. 1, part of inner core top surface is not coated by coating, and is exposed to surface of solid preparation.

Components and contents are as follows: 1000 tablets in total, each tablet weigh 800 mg.

| Inner core | |
| --- | --- |
| aripiprazole | 15 g |
| sodium alginate | 105 g |

-continued

| Inner core | |
|---|---|
| hydroxypropyl cellulose | 15 g |
| lactose | 159 g |
| magnesium stearate | 3 g |
| micro powder silica gel | 3 g |
| In total | 300 g |

| Coating | |
|---|---|
| aripiprazole | 5 g |
| Hydroxypropyl methyl cellulose K100LV | 170 g |
| lactose | 315 g |
| magnesium stearate | 5 g |
| micro powder silica gel | 5 g |
| In total | 500 g |

Preparation Method:

1. Raw materials of inner core are weighed according to above prescription, and mixed completely for the next step; two model numbers of punch pin are selected, and diameter of said model number I punch pin is less than that of model number II punch pin;

2. Rotary tablet press machine is used with model number I punch pin installed; filling depth and pressing force of tablet press machine are adjusted for pressing inner core; weight of inner core is 300 mg per piece, and inner core hardness is 90N;

3. Adjuvants for coating are weighed according to prescription, and mixed completely for the next step;

4. Rotary tablet press machine is used with model number II punch pin installed; process parameters of tablet press machine are adjusted; the pressed inner core is put in center of stamping die; then the mixed coating materials are filled for pressing tablet, to make bottom surfaces of bottom and side of inner core are coated by coating materials; total weight of tablet is 800 mg, and hardness is 100N.

Figure 6:
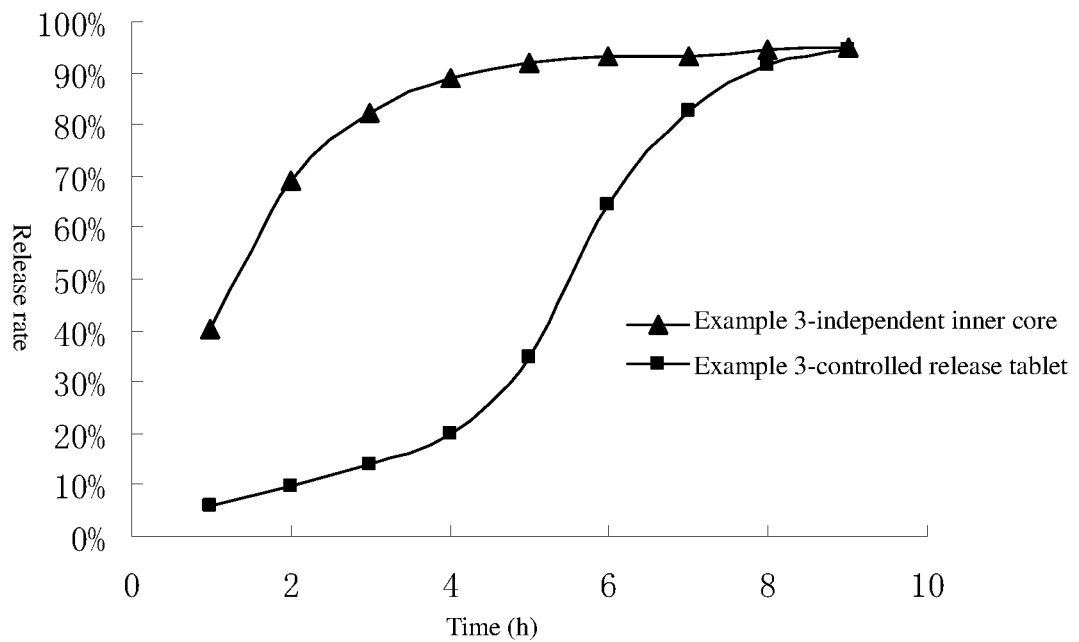

Medicine dissolution is detected, and dissolution curve is shown in FIG. 6. It's can be seen from FIG. 6 that, independent inner core disintegrates dissolve completely after 4 hours, and medicine release rate reach more than 90%. After controlled-release tablet with coating is prepared, medicine releases slowly in 4 hours; medicine release speed increases after 4 hours, and dissolution completes in 8 hours.

Tablet core in example 3 is mono-layer tablet. Coating contains active ingredients. The soluble hydroxypropyl cellulose is selected as coating material. In dissolution experiment, outer coating of tablet is dissolved gradually with active ingredients gradual releasing gradually, which remedies the problem of insufficient cumulative release amount due to medicine releasing only from top surface. After outer shell dissolves completely, tablet core is completely exposed to outside, and medicine begins to spread from all sides with medicine release amount enhanced. This medicine model can also be used as medicine for treating those diseases which outbreak easily in the early morning, and its effect is similar with that of example 2.

Example 4

Controlled Release Preparation with Inner Core of Two Layers (2 Sustained Release Layers)

Figure 3:
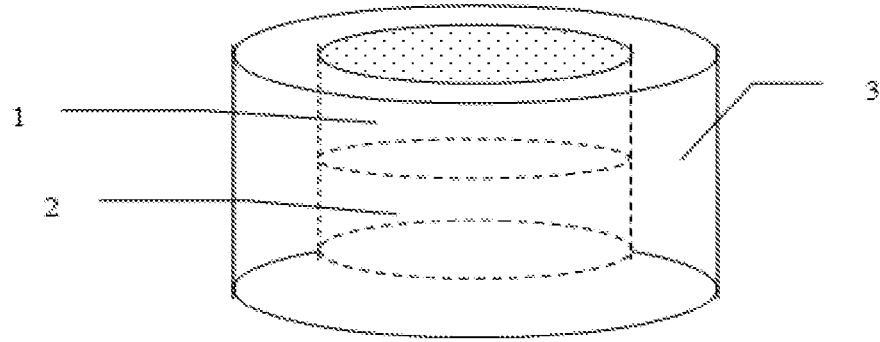
FIG. 3 is a structural diagram of controlled release tablet with another double layer tablet as inner core, wherein, 1 is inner core-sustained release $1^{st}$ layer; 2 is inner core-sustained release $2^{nd}$ layer; 3 is coating.

Preparation includes inner core and coating outside the inner core, and said inner core is double layer tablet consisting of sustained release layer 1 and sustained release layer 2. As shown in FIG. 3, part of inner core top surface is not coated by coating, and is exposed to surface of solid preparation.

Components and contents are as follows: 1000 tablet in total, each tablet weigh 800 mg.

| Inner core-sustained release layer 1 | |
|---|---|
| Lamotrigine | 30 g |
| Hydroxypropyl methyl cellulose K4M | 37.5 g |
| lactose | 79.5 g |
| magnesium stearate | 1.5 g |
| micro powder silica gel | 1.5 g |

| Inner core-sustained release layer 2 | |
|---|---|
| Lamotrigine | 30 g |
| Hydroxypropyl methyl cellulose K100LV | 52.5 g |
| Lactose | 66 g |
| Natural food color | 0.15 g |
| magnesium stearate | 1.05 g |
| In total | 300 g |

| Coating | |
|---|---|
| ethyl cellulose | 390 g |
| lactose | 100 g |
| magnesium stearate | 5 g |
| micro powder silica gel | 5 g |
| In total | 500 g |

Preparation Method:

1. Raw materials of inner core-sustained release layer 1, inner core-sustained release layer 2 are weighed according to above prescription, and mixed completely for the next step; two model numbers of punch pin are selected, and diameter of said model number I punch pin is less than that of model number II punch pin;

2. Rotary tablet press machine is used with model number I punch pin installed; filling depth and pressing force of tablet press machine are adjusted for pressing inner core; wherein, weights of inner core-sustained release layer 1, inner core-sustained release layer 2 are respectively 150 mg per piece, total weight of inner core is 300 mg per table, and inner core hardness is 90N;

3. Adjuvants for coating are weighed according to prescription, and mixed completely for the next step;

4. Rotary tablet press machine is used with model number II punch pin installed; technological parameters of tablet press machine are adjusted; the pressed inner core with the colored rapid release layer upwards is put in center of stamping die; then the mixed coating materials are filled for pressing tablet, to make bottom surfaces and side of inner core are completely coated by coating materials; total weight of tablet is 800 mg, and hardness is 100N.

Figure 7:
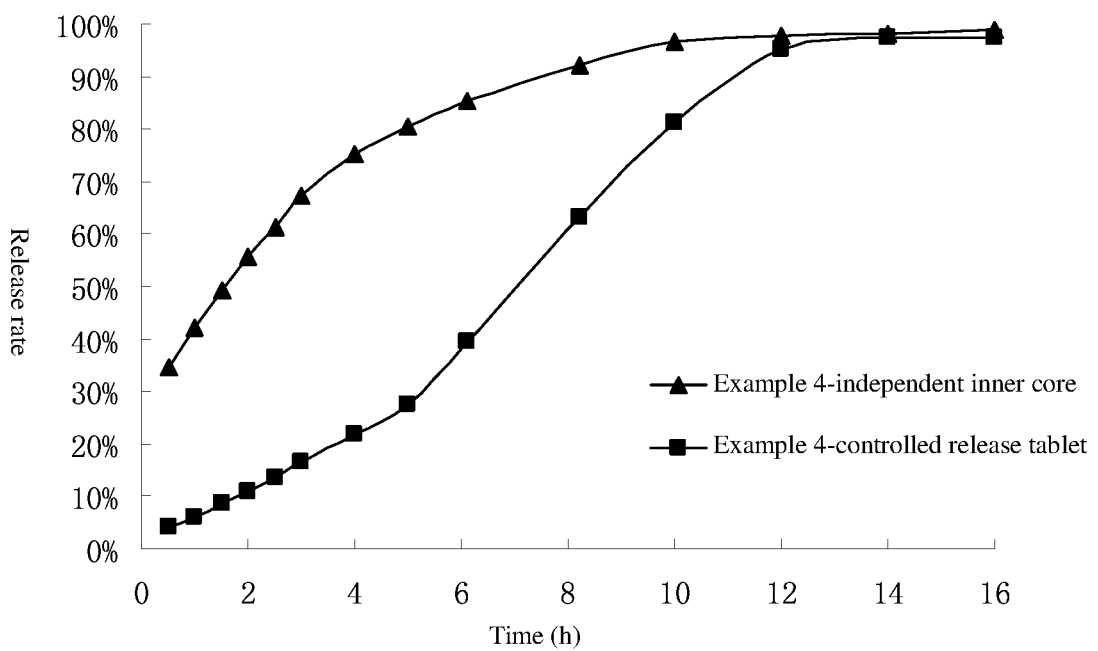

Medicine dissolution is detected, and dissolution curve is shown in FIG. 7. It's can be seen from FIG. 7 that, dissolution curve of independent inner core shows first order release with more than 30% released in 0.5 h, and cumulative dissolution rate in 10 hours is up to 90%. While, release of controlled-release tablet shows features of two stages: the first stage: slow release speed in 0-5 hours, and the second stage: release speed is coming fast in 5-12 h, but in these two stages, the release speeds are constant.

Tablet core in example 4 is double layer tablet consisting of two layers with two different release speed; release speed of the upper layer is slow, and that of the lower layer is fast.

Examples 5-10

Preparations of examples 5-10 is same as that of example 1. They are all preparations whose inner core is mono-layer (only one sustained release layer).

Components and contents are as follows: 1000 tablet in total, each tablet weigh 800 mg.

|  | Example 5 | Example 6 | Example 7 | Example 8 | Example 9 | Example 10 |
|---|---|---|---|---|---|---|
| Inner core |  |  |  |  |  |  |
| ibuprofen | 75 g | 75 g | 75 g | 75 g | 75 g | 75 g |
| hydroxypropyl methyl cellulose K100LV | 75 g | 75 g | 75 g | 105 g | 135 g | 45 g |
| Methyl cellulose | 15 g | 15 g | 15 g | 15 g | 15 g | 15 g |
| lactose | 129 g | 129 g | 129 g | 99 g | 69 g | 159 g |
| magnesium stearate | 3 g | 3 g | 3 g | 3 g | 3 g | 3 g |
| micro powder silica gel | 3 g | 3 g | 3 g | 3 g | 3 g | 3 g |
| In total | 300 g | 300 g | 300 g | 300 g | 300 g | 300 g |
| Coating |  |  |  |  |  |  |
| ethyl cellulose | 440 g | 465 g | 340 g | 390 g | 390 g | 390 g |
| lactose | 50 g | 25 g | 150 g | 100 g | 100 g | 100 g |
| magnesium stearate | 5 g | 5 g | 5 g | 5 g | 5 g | 5 g |
| micro powder silica gel | 5 g | 5 g | 5 g | 5 g | 5 g | 5 g |
| In total | 500 g | 500 g | 500 g | 500 g | 500 g | 500 g |

In addition, this invention also discloses the influence of amount for soluble component in outer coating of controlled-release tablet and the influence of amount for sustained-release materials in inner core on medicine dissolution, and the method is same as that of example 1.

Dissolution of tablets in example 1, example 5, example 6, example 7 are compared; it's can be seen from FIG. 8 that, the more content of soluble material—lactose in coating is, the faster coating dissolution speed is.

Dissolution of tablets in example 1, example 8, example 9, example 10 are compared; it's can be seen from FIG. 9 that, the more content of sustained release material in inner core is, the slower inner core dissolution speed is;

Example 11

Figure 10:
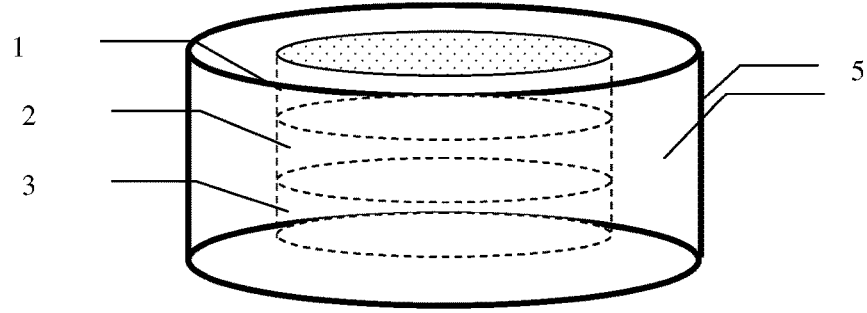
FIG. 10 is a structural diagram of controlled release tablet with three layers of inner core as inner core in example 12, wherein 1 is the upper layer of inner core containing medicine; 2 is the intermediate block layer of inner core; 3 is the lower layer of inner core containing medicine; 4 is coating containing medicine; 5 is outermost film coating containing medicine.

Inner core of controlled release preparation has three layers (each layer has active ingredient). Incomplete coating layer also has active ingredient, and the outermost film coating also has active ingredient. As shown in FIG. 10, part of medicine layer on upper layer of inner core is not coated by coating, and is exposed to surface of solid preparation.

Components and contents are as follows: 1000 tablet in total, each tablet weigh 800 mg.

| Upper core layer | |
|---|---|
| ropinirole hydrochloride | 0.5 |
| Hydroxypropyl methyl cellulose K100LV | 20 |
| microcrystalline cellulose | 15 |
| lactose | 61.5 |
| magnesium stearate | 1.5 |
| micro powder silica gel | 1.5 |

| Intermediate core layer | |
|---|---|
| ropinirole hydrochloride | 0.5 |
| Hydroxypropyl methyl cellulose K100lv | 35 |
| lactose | 62.5 |
| magnesium stearate | 1 |
| micro powder silica gel | 1 |

| Lower core layer | |
|---|---|
| ropinirole hydrochloride | 0.5 |
| Hydroxypropyl methyl cellulose K100LV | 25 |
| microcrystalline cellulose | 72.5 |
| magnesium stearate | 1 |
| micro powder silica gel | 1 |
| In total | 300 |

| Pressed coating layer | |
|---|---|
| duloxetine hydrochloride | 50 |
| ethyl cellulose | 340 |
| lactose | 100 |
| magnesium stearate | 5 |
| micro powder silica gel | 5 |
| In total | 500 |

| Film coating layer | |
|---|---|
| ropinirole hydrochloride | 0.25 |
| Opadry K295 coating powder | 15.75 |
| Water | Approriate amount |

Preparation Method:

1. Raw materials of upper layer, intermediate layer, lower layer of inner core are weighed according to above prescription, and respectively mixed completely for the next step; two model numbers of punch pin are selected, and diameter of said model number I punch pin is less than that of model number II punch pin;

2. Rotary tablet press machine is used with model number I punch pin installed; filling depth and pressing force of tablet press machine are adjusted for pressing inner core; wherein, weight of upper layer of inner core is 100 mg per piece; weight of intermediate layer is 100 mg per piece; weight of lower layer is 100 mg per piece; total weight of inner core is 300 mg, and inner core hardness is 100N;

3. Adjuvants for coating are weighed according to prescription, and mixed completely for the next step;

4. Rotary tablet press machine is used with model number II punch pin installed; process parameters of tablet press machine are adjusted; the pressed inner core with the colored rapid release layer upwards is put in center of stamping die; then the mixed coating materials are filled for pressing tablet, to make bottom surfaces of bottom and side of inner core are completely coated by coating materials; total weight of tablet is 800 mg, and hardness is 120N.

5. Coating powder is weighed according to prescription to prepare coating liquid. High efficiency coating machine is used to coat the outermost film coating, and weight of coating is increased 2%.

Figure 11:
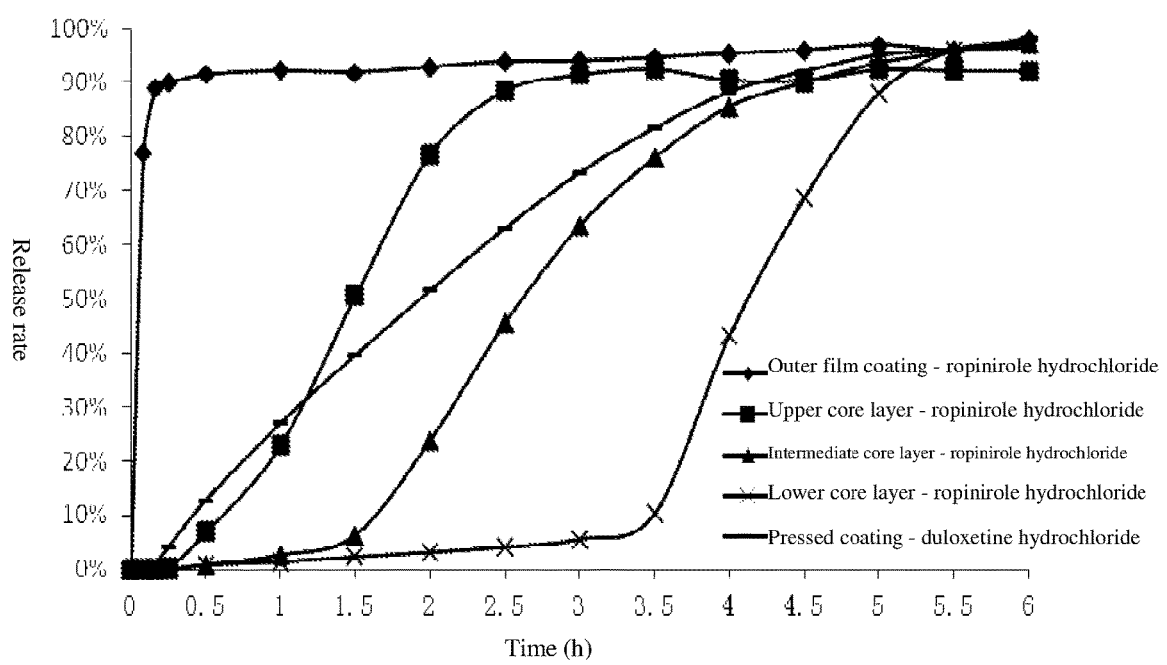
FIG. 11 is dissolution curve of controlled release tablet in example 12, which shows release pattern combining sustained release drug delivery and pulse type drug delivery.

Medicine dissolution is detected, and dissolution curve is shown in FIG. 11. It's can be seen from FIG. 11 that, medicine release shows pulse type; the outermost film coating releases medicine firstly; after 15 minutes, upper core layer begins to dissolve to release medicine; intermediate core layer begins to release medicine after 1.5 hours; lower core layer begins to release after 3.5 hours. Additionally, medicine in the pressed coating constantly releases during the whole dissolution process, after the outermost film coating dissolved.

The invention claimed is:

1. A controlled-release solid preparation, being a tablet and consisting of an inner core and a coating layer, said inner core containing an active medicine and an adjuvant, said coating layer containing a sustained release/controlled release material, said coating layer containing or not containing active medicine, characterized in that, a part of the top surface of said inner core is not coated by said coating layer and the bottom and side surfaces of said inner core are coated by said coating layer, and wherein the material of said coating layer is water-insoluble and comprises one or more selected from the group consisting of ethyl cellulose, a cellulose acetate polymer, and an acrylic resin, the material of coating layer also contains water-soluble pore-forming agent, which is selected from one or several of the groups consisting of povidone, lactose, sodium chloride.

2. The solid preparation according to claim 1, wherein said inner core is one layer or multi-layers, and said layer is a sustained release layer, or contains both a rapid release layer and a sustained release layer; and wherein when said inner core is two or more layers, components of different layers release in sequence: the outermost layer releases first, then the secondary outer layer releases, then at last the component of the innermost layer of said inner core releases.

3. The solid preparation according to claim 1, said coating layer is prepared by compression coating method.

4. The solid preparation according to claim 1, which comprises another coating layer on the outer surface of said coating layer, wherein said another coating layer contains or does not contain active ingredients.

5. The solid preparation according to claim 1, wherein said inner core is a tablet core consisting of one layer or more than one layer of tablet.

6. The solid preparation according to claim 1, said inner core has one layer; said layer is sustained release layer; wherein components and contents of said sustained release layer in per 1000 tablets are as follows:

ibuprofen 75 g, hydroxypropyl methyl cellulose K100LV 45-75 g, Methyl cellulose 15 g, lactose 129 g, magnesium stearate 3 g, micro powder silica gel 3 g;

components and contents of said coating layer in per 1000 tablets are as follows:

ethyl cellulose 390-465 g, lactose 250-150 g, magnesium stearate 5 g, micro powder silica gel 5 g.

7. The solid preparation according to claim 1, said inner core has one layer; said layer is sustained release layer; wherein components and contents of said sustained release layer in per 1000 tablets are as follows:

aripiprazole 15 g, sodium alginate 105 g, hydroxypropyl cellulose 15 g, lactose 159 g, magnesium stearate 3 g, micro powder silica gel 3 g;

components and contents of said coating layer in per 1000 tablets are as follows:

aripiprazole 5 g, hydroxypropyl methyl cellulose K100LV 170 g, lactose 315 g, magnesium stearate 5 g, micro powder silica gel 5 g.

8. The solid preparation according to claim 1, said inner core has two layers; components of different layers release in sequence: outermost layer releases first, then innermost layer releases; said outermost layer is sustained release layer; innermost layer is rapid release layer; wherein components and contents of said sustained release layer in per 1000 tablets are as follows: prednisolone acetate 20 g, hydroxypropyl methyl cellulose K4M 60 g, lactose 116 g, magnesium stearate 2 g, micro powder silica gel 2 g;

components and contents of said rapid release layer in per 1000 tablets are as follows:

prednisolone acetate 10 g, lactose 40 g, microcrystalline cellulose 44 g, cross-linked sodium carboxymethyl cellulose 5 g, lemon yellow 0.3 g, magnesium stearate 0.7 g;

components and contents of said coating layer in per 1000 tablets are as follows:

ethyl cellulose 390 g, lactose 100 g, magnesium stearate 5 g, micro powder silica gel 5 g.

9. The solid preparation according to claim 1, said inner core has two layers; components of different layers release in sequence: outermost layer releases first, then innermost layer releases; said outermost layer is sustained release layer 1; innermost layer is sustained release layer 2; wherein components and contents of said sustained release layer 1 in per 1000 tablets are as follows: Lamotrigine 30 g, Hydroxypropyl methyl cellulose K4M 37.5 g, lactose 79.5 g, magnesium stearate 1.5 g, micro powder silica gel 1.5 g;

components and contents of said sustained release layer 2 in per 1000 tablets are as follows: Lamotrigine 30 g, Hydroxypropyl methyl cellulose K100LV 52.5 g, lactose 66 g, natural food color 0.15 g, magnesium stearate 1.05 g;

components and contents of said coating layer in per 1000 tablets are as follows:

ethyl cellulose 390 g, lactose 100 g, magnesium stearate 5 g, micro powder silica gel 5 g.

10. The solid preparation according to claim 2, which comprises another coating layer on the outer surface of said coating layer, wherein said another coating layer contains or does not contain active ingredients.

11. The solid preparation according to claim 3, which comprises another coating layer on the outer surface of said coating layer, wherein said another coating layer contains or does not contain active ingredients.

12. The solid preparation according to claim 2, wherein said inner core contains multiple layers including both a rapid release layer and a sustained release layer.

13. The solid preparation according to claim 2, wherein said inner core contains multiple layers, and components of different layers release in sequence: the outermost layer releases first, then the secondary outer layer releases, then at last the component of the innermost layer of said inner core releases.

14. The solid preparation according to claim 1, wherein the tablet is prepared in a tablet press machine by using two punch pins of different sizes, by following steps:
   1) mixing all the components for preparing the inner core, and the first pressing is performed by using model number I punch pin to obtain the inner core;
   2) putting the inner core in the center of a middle module firstly, then filing the uniformly mixed coating layer components around the inner core and performing the second pressing by using model number II punch pin,
   wherein the diameter of the model number I punch pin is less than that of model number II punch pin.

15. The solid preparation according to claim 1, wherein the coating layer weight is more than that of inner core in the tablet.

16. The solid preparation according to claim 1, wherein weight ratio between the inner core and coating layer is 3:5.

17. The solid preparation according to claim 1, said coating layer contains 5-30%, 20-30% or 20% weight ratio water-soluble pore-forming agent.

\* \* \* \* \*